US008770202B2

(12) United States Patent
Röhrig

(10) Patent No.: US 8,770,202 B2
(45) Date of Patent: Jul. 8, 2014

(54) NIPPLE PROTECTION DEVICE FOR BREAST-FEEDING MOTHERS

(75) Inventor: Peter Röhrig, Vienna (AT)

(73) Assignee: Bamed AG, Woolerau (CH)

( * ) Notice: Subject to any disclaimer, the term of this patent is extended or adjusted under 35 U.S.C. 154(b) by 644 days.

(21) Appl. No.: 11/324,883

(22) Filed: Jan. 4, 2006

(65) Prior Publication Data

US 2006/0157065 A1 Jul. 20, 2006

(30) Foreign Application Priority Data

Jan. 20, 2005 (AT) .............................. GM28/2005 U

(51) Int. Cl.

| | |
|---|---|
| ***A61J 13/00*** | (2006.01) |
| ***A61F 13/00*** | (2006.01) |
| ***A61J 9/00*** | (2006.01) |
| ***A61J 11/00*** | (2006.01) |

(52) U.S. Cl.
USPC .......... 128/890; 215/11.1; 215/11.4; 128/889

(58) Field of Classification Search
CPC ......... A61J 13/00; A61J 11/00; A61J 11/005; A01K 9/005; A01K 39/0213; A61M 2001/068
USPC .................. 128/890; 215/11.4; 606/234, 236; D24/194, 196, 199; 426/117; 220/717, 220/714; 2/104; 450/37; 251/12, 82
See application file for complete search history.

(56) References Cited

U.S. PATENT DOCUMENTS

| | | | | | |
|---|---|---|---|---|---|
| 2,364,866 | A | * | 12/1944 | Meynier, Jr. | 128/890 |
| 4,195,639 | A | * | 4/1980 | Lee | 450/57 |
| 4,946,062 | A | * | 8/1990 | Coy | 220/714 |
| 5,403,349 | A | * | 4/1995 | Rohrig | 606/234 |
| 5,730,336 | A | * | 3/1998 | Lerner | 222/490 |
| 5,797,505 | A | * | 8/1998 | Kaura | 215/11.5 |
| 6,027,396 | A | * | 2/2000 | Yonchar | 450/36 |
| 6,161,710 | A | * | 12/2000 | Dieringer et al. | 215/11.4 |
| 6,968,964 | B2 | * | 11/2005 | Gilmore | 215/11.1 |
| 7,175,502 | B2 | * | 2/2007 | Clark | 450/37 |
| 2004/0220618 | A1 | * | 11/2004 | Rohrig | 606/234 |
| 2005/0145636 | A1 | * | 7/2005 | Albright et al. | 220/714 |

FOREIGN PATENT DOCUMENTS

| | | |
|---|---|---|
| DE | 44 15 939 | 1/1996 |
| DE | 202 19 950 | 3/2003 |
| WO | WO 2005/077264 | 8/2005 |

* cited by examiner

*Primary Examiner* — Victoria J Hicks
(74) *Attorney, Agent, or Firm* — Ladas & Parry LLP

(57) ABSTRACT

A nipple protection device for breast-feeding mothers having a nipple portion projecting upwardly from an arched shield portion. The nipple portion is provided with at least one drinking opening at its front side. The nipple portion is of generally oval cross-section and the at least one drinking opening is formed by at least one longitudinal slit.

14 Claims, 2 Drawing Sheets

NIPPLE PROTECTION DEVICE FOR BREAST-FEEDING MOTHERS

This application claims the benefit of GM 28/2005, filed in Austria on Jan. 20, 2005.

The invention relates to a nipple protection device for breast-feeding mothers, which nipple protection device comprises a nipple portion projecting upwardly from an arched shield portion, the nipple portion being provided with at least one drinking opening at its front side.

Both, for mothers and also for the infant it is important that breast-feeding is free from stress and relaxing. Often, however, the start of breast-feeding or the breast-feeding procedure, respectively, is rendered difficult due to a poor sucking power of the infant or because the infant is a lazy feeder, due to the mother's lack of self-confidence or because the infant does not grab the mother's natural nipple well, due to organic malformations of the infant, because of special, peculiar shapes of the mother's natural nipple, such as plane or sunken nipples, due to an unfavorable milk flow reflex, because sucking of the infant causes pain to the mother, due to galactostasis, because of the mother's affinity to wounds or to chapped nipples or to an inflammation of the breast (mastitis), in the worst case.

In case of such difficulties or, quite generally, for breast feeding, so-called nipple protection devices or breast-feeding protection devices or nursing pads are used as auxiliary means, which are put over the nipple, over the areola or over part of the mother's breast for the breast-feeding procedure, in which case the infant will suck directly on the protection device.

Nipple protection devices of the initially defined type are known from DE 202 19 950 U1, DE 44 15 939 C1 and U.S. Pat. No. 2,364,866 A. These nipple protection devices for breast-feeding mothers consist of a thin-walled, supple material and have a large-area rim of e.g. circular or triangular shape with rounded corners, seen in top view. The sucking nipple of circular cross-section which projects upwardly from the base or shield portion, has drinking holes at its front face. When handling this nipple protection device it has, however, been found out that the drinking holes are not optimal for an unimpeded flow of milk during sucking. During the sucking procedure, the infant draws the nipple protection device, or the mother's natural nipple, respectively, comparatively deeply into his/her mouth so that it is "clamped" between palate and tongue, whereby also the circular cross-section of the nipple protection device is compressed. Thus, it may happen that the drinking holes are pressed together and the milk cannot flow freely through the holes. The milk already emerged accumulates between the mother's breast and the nipple protection device and may adversely affect the adherence of the nipple protection device on the mother's breast. There is a risk of the nipple protection device becoming unintentionally detached from the breast, which may not only have consequences for the sensitive skin of the natural nipple and the areola, but also entails the risk of the infant swallowing the nipple protection device with his/her natural sucking reflex.

It is now an object of the present invention to provide a nipple protection device of the aforementioned type, with which sucking of the mother's milk during breast-feeding will be facilitated for the infant and be rendered possible without any impediment, wherein such sucking shall also be gentle for the mother's breast itself.

The nipple protection device according to the invention of the initially defined type is characterized in that the nipple portion is of generally oval cross-section and in that the at least one drinking opening is formed by at least one longitudinal slit. The nipple portion of generally oval cross-section has a "flat" shape which is favorable for sucking in the first place, by which also the position during sucking is pre-determined, and at the same time a good adaptation of the nipple portion to the mother's natural nipple is provided. For the sucking procedure, the infant moves his/her tongue from bottom to top and "pulls out" the mother's milk from the mother's breast at the same time, using the sucking reflex and the vacuum in the infant's mouth. The cross-section of oval shape which is adapted to the natural oval shape of the lips and mouth of the infant therefore can be pressed together without any problems by the sucking movements of the infant, whereby furthermore, the drinking opening formed by the longitudinal slit is widened in a simple manner and thus will ensure an unimpeded flow of milk. It has been shown that opening of the longitudinal slit will be ensured in any event if the longitudinal slit is arranged in the region of the middle of the front part of the nipple portion.

Advantageously, the longitudinal slit extends transversely to the longer axis of the generally oval nipple portion cross-section. By this arrangement, the longitudinal slit will "automatically" widen to the extent desired as soon as the nipple portion is pressed together by the infant's sucking movement. Thus, also breast-feeding which is gentle for the mother's breast itself is enabled.

According to an alternative, preferred embodiment, two longitudinal slits are provided on both sides of an imaginary nipple portion middle plane. This embodiment has proved to be advantageous for withdrawing an amount of milk to an optimum extent. Also in case of a possible movement of the infant's head or mouth, respectively, undisturbed breast-feeding is made possible. In the embodiment exhibiting two longitudinal slits, the length thereof may be comparatively shorter.

It has proved to be suitable if the longitudinal slit(s) has (have) a length of from 4 mm to 8 mm. Since various sizes of nipple protection devices may be provided, the sizes of the drinking opening(s) can be adapted to the size of the nipple protection device and chosen according to the number of longitudinal slits. (Of course, also more than two longitudinal slits may be provided in the nipple portion).

Preferably, the nipple portion of generally oval cross-section has a rough surface at least on one of its longer side faces. The rough surface has the effect that the nipple portion in these regions will have a skin-like feel, similar to that of a mother's breast. Accordingly, it is furthermore suitable if regions with a rough surface are provided on both longer side faces. Moreover, it is advantageous for the nipple portion to have a rough surface on its front side. By this, the infant will feel a soft, skin-like object not only on his/her tongue and upper jaw, but also in the region of his/her palate.

In order to obtain a good imitation of the skin-like texture of a female nipple and areola, it is suitable if the surface roughness of the side faces and/or of the front side of the nipple portion is 100 μm at the most, in particular 50 μm at the most. Tests have shown that for the desired texture it is particularly advantageous if the zone with the rough surface has a surface roughness of approximately 10 μm to approximately 40 μm, preferably 15 μm to 30 μm.

Likewise, the surface of the shield portion may be formed with a texture similar to that of a mother's natural nipple. In particular, it is advantageous if the shield portion has outwardly projecting knobs. Upon contact with the infant's lips or cheeks, these knobs can convey a pleasant feeling.

For good handling of the nipple protection device during its application and removal, respectively, it is suitable if the shield portion is lemniscate-shaped, wherein the longer axis of the shield portion lemniscate extends in parallel to the longer axis of the nipple portion cross-section. By this specific shape having narrowed portions on account of the lemniscate shape, the nipple protection device can be gripped easily and securely and applied to the front breast in the correct orientation and after the breast-feeding procedure, it can also be grasped well and taken off.

With regard to the material of the nipple protection device, it has been found suitable to make the shield portion and the nipple portion—in one piece—of silicone caoutchouc. This material is tasteless, fits snugly to the breast of the breast-feeding mother, is simple to process and meets the requirements of hygiene. Another preferred material is latex or a thermo-plastic elastomer.

In connection with a good/soft fit of the nipple protection device it is advantageous if the material of the shield portion and/or of the nipple portion has a Shore hardness A of at least 40.

Preferably, a wall thickness of the shield portion and/or of the nipple portion of from 0.9 mm to 1.50 mm is chosen; a wall thickness of 1.20 mm has proved particularly suitable.

In the following, the invention will be explained in more detail by way of preferred exemplary embodiments illustrated in the drawings.

Therein, FIG. 1 shows a perspective view of a nipple protection device according to the invention;

Figure 1:
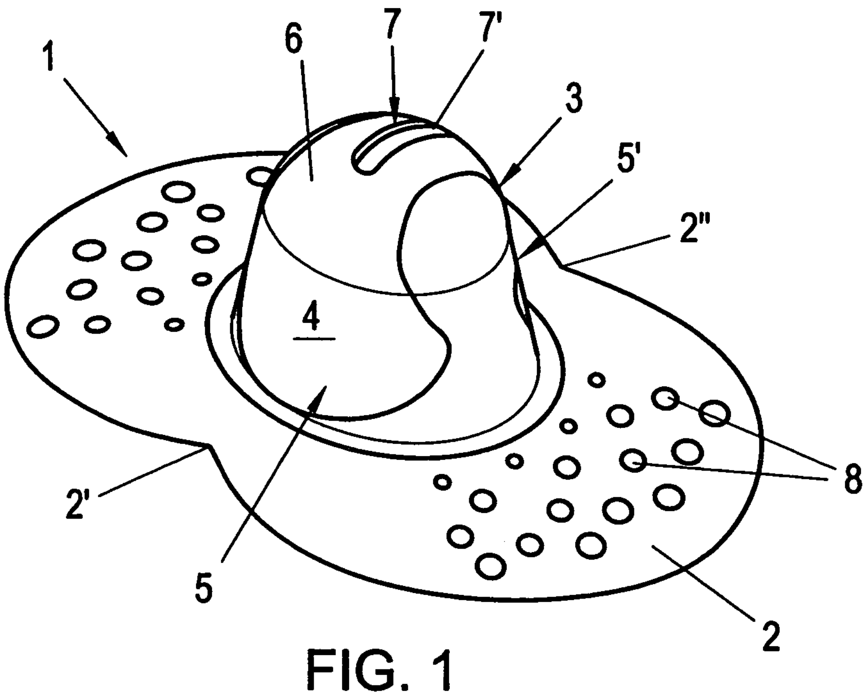

FIG. 1 shows in a perspective view a single-piece nipple protection device 1 having an arched base or shield portion 2 and a nipple portion 3 projecting upwards therefrom. The shield portion 2 is formed to be lemniscate-shaped, as is particularly visible from FIG. 3, while the nipple portion 3, seen in cross-section, has a generally oval shape which substantially corresponds to the shape of a mother's natural nipple during drinking, or to the (elongate) shape of the mouth of an infant, respectively. The nipple portion 3 has a rough surface 4 which here extends over both longer side faces 5, 5' as well as over the front side 6.

On the front side 6, a drinking opening 7 is provided which is formed by a longitudinal slit 7' that extends transversely to the longer axis of the nipple portion 3 of generally oval cross-section. During sucking, the nipple portion 3 will be pressed or slightly squeezed, respectively, by the tongue and the upper jaw of the infant, whereby the longitudinal slit 7' will slightly widen and the milk will be able to pass through the drinking opening 7 without impediment.

At its outer side (which faces the infant during use), the shield portion 2 illustrated has protruding knobs 8. Preferably, the knobs 8 have different sizes and are only provided in the wider regions of the lemniscate-shaped shield portion 2. The knobs 8 may, however, also be distributed over the entire surface of the shield portion 2, and their arrangement may be random or regular.

Figure 2:
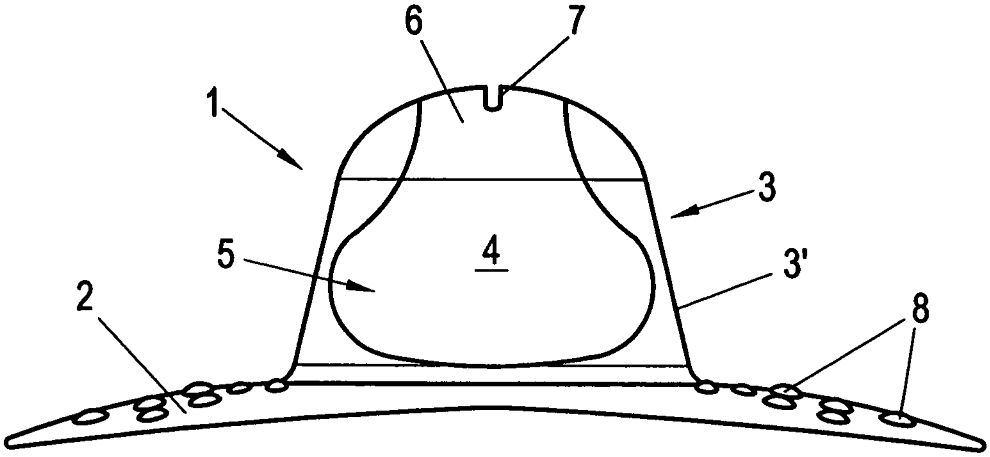
FIG. 2 shows an elevational view of this nipple protection device according to FIG. 1.

As is particularly visible in FIG. 2, the nipple portion 3 has a conical nipple shaft 3' which passes into the hood-shaped front side 6. As it is visible, the rough surface 4 is designed to be wider on the nipple shaft 3' as compared to the front side 6 of the nipple portion 3.

The longitudinal slit 7' provided on the front side 6 extends transversely to the longer axis 3" of the generally oval nipple portion cross-section.

Moreover, it is visible from FIGS. 1 and 2 that the nipple shaft 3' continuously merges into the shield portion 2 and the shield portion 2 is slightly arched downwardly, resulting in an improved fit of the nipple protection device 1 so that it will be well seated on the female breast. The lemniscate shape of the shield portion 2 provides for two oppositely located narrowed portions 2', 2" which are suitable for gripping the nipple protection device 1 for attaching or detaching the same, respectively.

Figure 3:
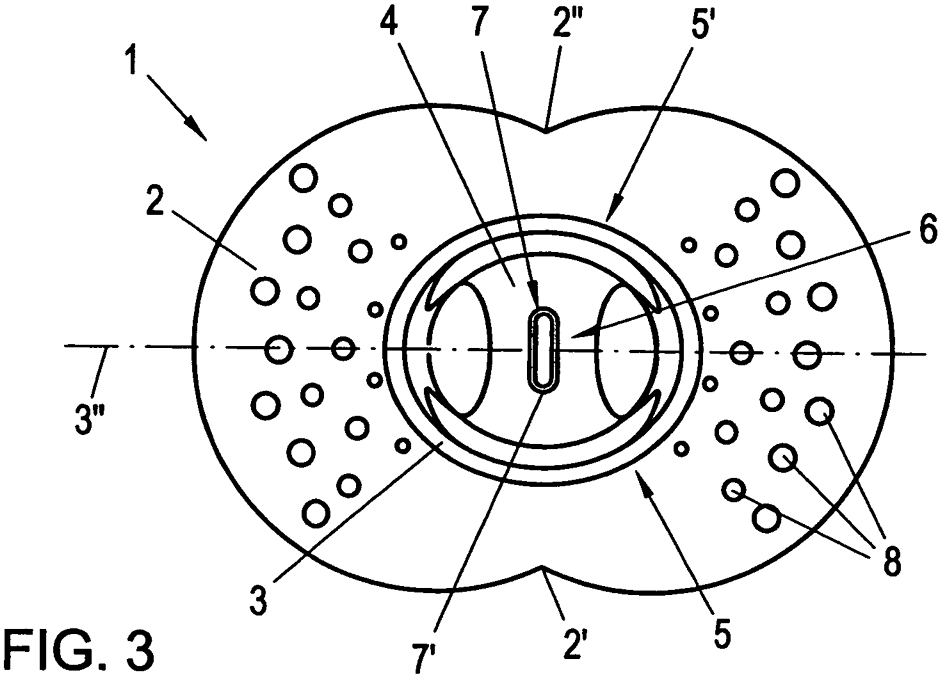
FIG. 3 shows a top view on the nipple protection device according to FIGS. 1 and 2.

As it is visible from FIG. 3, the lemniscate shape of the shield portion 2 is provided such that its longitudinal axis corresponds to the longer axis 3" of the nipple portion 3 of oval cross-section, seen in top view. The narrowest site of the shield portion 2 is advantageously located on one line with the longitudinal slit 7 formed on the front side 6 of the nipple portion 3. At its narrowest site, the shield portion 2 has a size of approximately 40 mm to approximately 50 mm, advantageously approximately 42 mm. The widest site of the shield portion 2 is approximately 45 mm to 50 mm, preferably approximately 49 mm, and its length is approximately 70 mm to 75 mm, preferably close to 74 mm. The nipple protection device 1 has a total height of e.g. from 25 mm to 30 mm, in particular approximately 27 mm. The dimensions of the shield portion 2, and also of the nipple portion 3, may vary depending on the size of the nipple protection device.

In the embodiment according to FIGS. 1 to 3, the longitudinal slit 7' is located substantially in the middle of the front side 6 of the nipple portion 3, wherein, as has been mentioned, it extends transversely to the longer axis 3" of the nipple portion 3. Thus, it is located midst the region having the rough surface 4 which extends up to the two side faces 5, 5' of the nipple portion 3 and of the nipple shaft 3', respectively.

Figure 4:
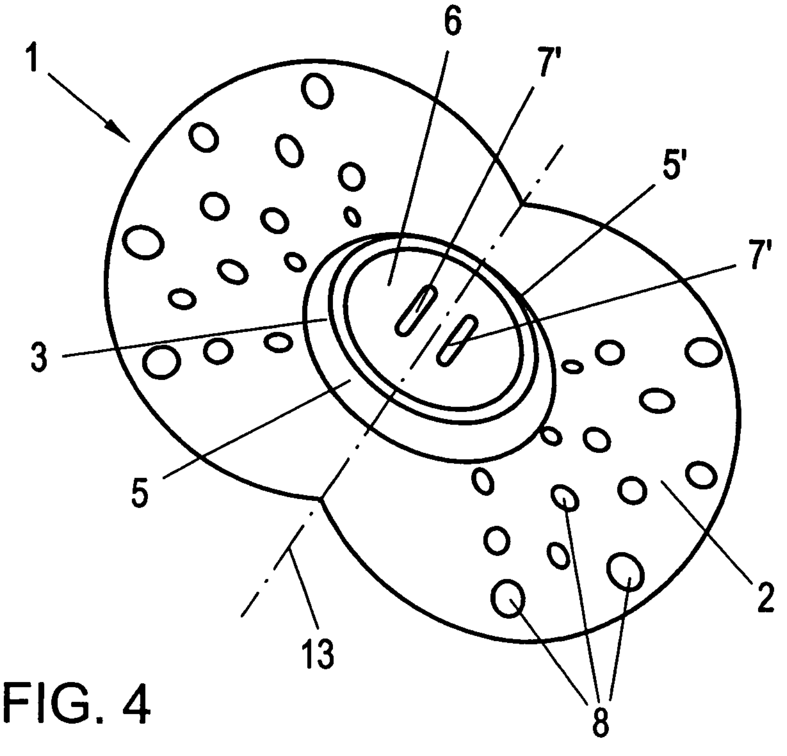
FIG. 4 shows a perspective view of a modified exemplary embodiment of the nipple protection device.

FIG. 4 shows an embodiment of the nipple protection device 1 in a perspective view, in which, in contrast to the nipple protection device 1 according to FIGS. 1 to 3, the front side 6 of the nipple protection device 1 has two longitudinal slits 7' provided as drinking openings 7. These longitudinal slits 7' are arranged on both sides of an imaginary nipple portion middle plane 13 that extends in accordance with the shorter axis of the nipple portion 3 which, again, is of generally oval shape, seen in cross-section. If desired, even more, i.e. three or more, longitudinal slits may be provided as the drinking openings 7. According to FIG. 4, furthermore, a rough surface 4 is only provided at the front side 6 of the nipple portion 3; of course, however, also the two longer side faces 5,5' of the nipple portion 3 may be rough.

The position of the longitudinal slits 7' substantially in the region of the middle of the front side 6 allows for a "centered" passage of the milk. Insofar, also the two longitudinal slits 7' according to FIG. 4 are relatively close to each other so as to prevent difficult sucking and swallowing for the infant.

The surface roughness may be 100 μm at the most, in particular 50 μm at the most, and is preferably within a range of approximately 10 μm to 40 μm, preferably from 15 μm to 30 μm.

The material thickness of the shield portion 2 and of the nipple portion 3 is approximately from 0.9 mm to 1.5 mm, in particular 1.2 mm. As for the material, preferably silicone caoutchouc or latex is chosen, wherein a Shore-A hardness of at least 40, preferably approximately 50, is provided.

The invention claimed is:

1. A nipple protection device for a breast-feeding mother which comprises a nipple portion of oval cross-section with a first, shorter extension in direction of a first cross-sectional axis and a second, longer extension in direction of a second cross-sectional axis, the nipple portion projecting upwardly from a shield flange portion, the shield flange portion having a concavely arched surface which is intended to be put over an areola, the nipple portion substantially corresponding to and being adapted to surround the shape of a nipple for adaptation of the nipple portion to the nipple, the nipple portion being provided with at least one drinking opening at its front side, wherein the at least one drinking opening has an unobstructed through hole and is formed by at least one longitudinal slit such that the at least one drinking opening is partially defined by two straight edges being arranged distant and parallel to each other, wherein the at least one longitudinal slit has a length of from 4 mm to 8 mm, wherein the at least one drinking opening extends in direction of the first cross-sectional axis and transversely to the second cross-sectional axis of the nipple portion of oval cross section, wherein the at least longitudinal slit is configured to be positioned over a front or end of the nipple and is configured to, during sucking, pass milk there through without impediment while the front or end of the nipple remains positioned under the at least one longitudinal slit, wherein as a result of the at least one drinking opening extending transversely to the second cross-sectional axis the at least one drinking opening is configured to automatically widen to an extent desired as soon as the nipple portion of oval cross-section is pressed together by an infant's sucking movement.

2. A nipple protection device according to claim 1, wherein the nipple portion of oval cross-section has a rough surface at least on one of its longer side faces.

3. A nipple protection device according to claim 1, wherein the nipple portion has a rough surface on a front side.

4. A nipple protection device according to claim 2 or 3, wherein a surface roughness of side faces and/or of a front side of the nipple portion is 100 μm at the most.

5. A nipple protection device according to 4, wherein the surface roughness of the side faces and/or of the front side of the nipple portion is 50 μm at the most.

6. A nipple protection device according to claim 5, wherein the surface roughness is 10 μm to 40 μm.

7. A nipple protection device according to claim 1, wherein the shield portion has outwardly projecting knobs.

8. A nipple protection device according to claim 7, wherein a surface roughness is 15 μm to 30 μm.

9. A nipple protection device according to claim 1, wherein the at least one longitudinal slit comprises two longitudinal slits are being provided on both sides of a nipple portion middle plane.

10. A nipple protection device according to claim 1, wherein the shield portion is lemniscate-shaped with a first, shorter dimension in direction of a first axis and a second, longer dimension in direction of a second axis, wherein the second axis of the shield portion extends in parallel to the second cross-sectional axis of the cross-section of the nipple portion.

11. A nipple protection device according to claim 1, wherein the shield portion and the nipple portion are made of silicone caoutchouc.

12. A nipple protection device according to claim 1, wherein the shield portion and the nipple portion are made of a material having a Shore-hardness A of at least 40.

13. A nipple protection device according to claim 1, wherein the shield portion and/or the nipple portion have a wall thickness of from 0.9 mm to 1.5 mm.

14. A nipple protection device according to claim 1, wherein the shield portion and for the nipple portion have a wall thickness of 1.2 mm.

* * * * *